United States Patent
Garrido (10) Patent No.: US 11,304,737 B1
(45) Date of Patent: Apr. 19, 2022

(54) PLACEMENT JIGS FOR OSTEOSYNTHESIS SYSTEMS AND RELATED METHODS

(71) Applicant: DESIGN ENTERPRISES, LLC, Cornelius, NC (US)

(72) Inventor: Benito J. Garrido, Cornelius, NC (US)

(73) Assignee: Design Enterprises, LLC, Cornelius, NC (US)

( * ) Notice: Subject to any disclaimer, the term of this patent is extended or adjusted under 35 U.S.C. 154(b) by 0 days.

(21) Appl. No.: 17/248,676

(22) Filed: Feb. 2, 2021

Related U.S. Application Data (60) Provisional application No. 63/115,612, filed on Nov. 19, 2020.

(51) Int. Cl.
| | |
|---|---|
| A61B 17/80 | (2006.01) |
| A61B 17/70 | (2006.01) |
| A61B 17/88 | (2006.01) |
| A61F 2/44 | (2006.01) |
| A61B 17/56 | (2006.01) |

(52) U.S. Cl.
CPC ........ *A61B 17/808* (2013.01); *A61B 17/7059* (2013.01); *A61B 17/88* (2013.01); *A61B 17/8872* (2013.01); *A61F 2/4455* (2013.01); *A61B 2017/564* (2013.01)

(58) Field of Classification Search
CPC . A61B 17/7059; A61B 17/80; A61B 17/8061; A61B 17/808; A61B 17/88; A61B 17/8872; A61B 17/90; A61F 2/4455
See application file for complete search history.

(56) References Cited

U.S. PATENT DOCUMENTS

| | | | |
|---|---|---|---|
| 7,591,853 B2 * | 9/2009 | Felt | A61F 2/442 606/249 |
| 7,815,681 B2 | 10/2010 | Ferguson | |
| 8,945,227 B2 * | 2/2015 | Kirschman | A61B 17/70 623/17.16 |
| 2007/0161962 A1 * | 7/2007 | Edie | A61M 25/0662 604/257 |
| 2016/0235448 A1 * | 8/2016 | Seex | A61F 2/4611 |
| 2019/0321197 A1 * | 10/2019 | Donaldson | A61B 17/808 |

* cited by examiner

*Primary Examiner* — Larry E Waggle, Jr.
(74) *Attorney, Agent, or Firm* — Stephen R. Bylciw, Esq.

(57) ABSTRACT

Placement jigs for osteosynthesis systems and related methods are disclosed. Medical intervention may require fusing vertebrae of a diseased spinal column together. This often includes securing an interbody within an intervertebral space and anchoring an anterior cervical plate to the vertebrae. A placement jig may be received through the plate, removably coupled to the secured interbody with a press fit coupling, and used to abut the plate against the vertebrae to hold desired plate positioning so the plate may be anchored to the vertebrae with precision. By positioning the plate relative to the interbody using the placement jig, higher stress concentrations causing undesirable loosening associated with a misaligned plate may be avoided. In this manner, the useful life of the plate within a patient may be lengthened.

20 Claims, 8 Drawing Sheets

PLACEMENT JIGS FOR OSTEOSYNTHESIS SYSTEMS AND RELATED METHODS

CROSS-REFERENCES TO RELATED APPLICATION

This application claims benefit of U.S. Provisional Patent Ser. No. 63/115,612 filed on Nov. 19, 2020 and entitled "SURGICAL POSITIONING DEVICES FOR ANTERIOR CERVICAL PLATES," which is incorporated herein by reference in its entirety.

BACKGROUND

Field of the Disclosure

The technology of the disclosure relates to osteosynthesis assemblies and methods for connecting bones to each other in an animal, such as a human.

Technical Background

A vertebral column and a spinal cord of a patient extend from the skull to the pelvis and form a longitudinal axis of a patient. The column includes vertebra that are separated by fibrocartilage structures (intervertebral disks) that are interconnected with ligaments. The vertebral column protects the spinal cord and provides structural support for the patient. The spinal cord along with a bundle of nerve fibers extending from the spinal cord form a central nervous system enabling communication between the brain and other parts of the patient. The spinal cord is protected within a vertebral canal formed by openings in each of the vertebrae. The vertebral column typically facilitates movement of the patient by enabling relative movement between adjacent vertebrae and often functions without issues, but medical intervention may involve fusing various vertebrae together in a process of stabilization to reduce pain or otherwise facilitate healing or improve quality of life.

In some interventions, interbody cages and anterior cervical plates may be used as part of an anterior arthrodesis for stabilization purposes. Early during the intervention, interbody cages are often implanted within the intervertebral spaces to replace diseased intervertebral discs. The cages are secured to endplates of the adjacent vertebrae. These cages may restore the proper spacing between vertebrae and may facilitate the eventual fusing together of the adjacent vertebrae with new bone structures. Later during the intervention, anterior cervical plates may be secured to anterior surfaces of these vertebrae using anchors to provide further stability. The combination of the cages and the plates are meant to provide adequate stability to prevent movement between the vertebrae that may cause patient discomfort and hinder desired bone fusion.

One drawback of conventional anterior cervical plates is that they can be difficult to accurately place in in a desired position and to maintain this position prior to anchoring. Correct positioning is advantageous as sub-optimal positioning of the plate may be one factor causing bone anchors to become loose over time and thereby defeat their purpose of providing stability. Accordingly, improvements are needed to better position cervical plates during implantation to prevent bone anchor loosening.

SUMMARY OF THE DETAILED DESCRIPTION

Embodiments disclosed herein include placement jigs for osteosynthesis systems and related methods. Medical intervention may require fusing vertebrae of a diseased spinal column together. This often includes securing an interbody within an intervertebral space and anchoring an anterior cervical plate to the vertebrae. A placement jig may be received through the plate, removably coupled to the secured interbody with a press fit coupling, and used to abut the plate against the vertebrae to hold desired plate positioning so the plate may be anchored to the vertebrae with precision. By positioning the plate relative to the interbody using the placement jig, higher stress concentrations causing undesirable loosening associated with a misaligned plate may be avoided. In this manner, the useful life of the plate within a patient may be lengthened.

In this regard, an osteosynthesis system is disclosed including an anterior cervical plate having a plate body and a placement jig having a jig body. The plate body includes a rear surface configured to abut against first and second vertebrae, a front surface opposite the rear surface, and a plate inner surface connecting the front and rear surfaces, wherein the plate inner surface forms a plate passageway. The jig body includes a distal portion, a proximal portion, and a medial portion. The distal portion includes a press fit surface configured to be received through the plate passageway and to be removably coupled to an interbody inner surface by a press fit coupling, wherein the interbody inner surface forms a recess of an interbody, and wherein the interbody is disposed within an intervertebral space and secured to the first and second vertebrae. The proximal portion includes lateral contact surfaces having a lateral width configured to be larger than a lateral width of the plate passageway and the proximal portion configured to abut against the plate body. The medial portion connects the distal portion to the proximal portion and is configured to be received through the plate passageway. In this manner, the alignment of the anterior cervical plate provided by the placement jig reduces the chance that the plate will slip out of position, for example while the surgeon is awling holes for the bone anchors. The placement jig facilitates optimal placement of the plate and positively aligns the cephalad anchors (i.e. the anchors nearer the patient's head) close to the corner edge of the first vertebra. This allows the surgeon to select a plate with a smaller vertical extent (i.e. vertical height), maximizing the distance between the top of the plate and the next disc above it, which serves as a mechanism for reducing the chance of adjacent level disc degeneration.

Another embodiment is disclosed that includes a placement jig having a distal portion, a proximal portion, and a medial portion. The distal portion including a press fit surface configured to be received through a plate passageway of an anterior cervical plate and to be removably coupled by a press fit coupling to an interbody inner surface of an interbody, wherein the interbody is disposed in an intervertebral space and secured to first and second vertebrae. The proximal portion including lateral contact surfaces having a lateral width configured to be larger than a lateral width of the plate passageway and the proximal portion configured to abut against a plate body of the anterior cervical plate, wherein the plate body includes a rear surface configured to abut against the first and the second vertebrae, a front surface opposite the rear surface, and plate inner surface connecting the front and rear surfaces, wherein the plate inner surface forms the plate passageway. The medial portion connects the distal portion to the proximal portion and configured to be received through the plate passageway. In this manner, the anchors may be more precisely implanted within the vertebrae.

In another embodiment, a method is disclosed. This method may include receiving a distal portion of a jig body of a placement jig through a plate passageway of an anterior cervical plate, wherein a plate body of the anterior cervical plate includes a rear surface configured to abut against first and second vertebrae, a front surface opposite the rear surface, plate inner surface connecting the front and rear surfaces, and the plate inner surface forms the plate passageway. The method may further include removably coupling, by a press fit coupling, a press fit surface of the distal portion to an interbody inner surface of an interbody, wherein the interbody is disposed in an intervertebral space and secured to the first and the second vertebrae. The method may also include abutting lateral contact surfaces of a proximal portion of the placement jig against the plate body, wherein the proximal portion includes a lateral width larger than a lateral width of the plate passageway, wherein a medial portion connects the distal portion to the proximal portion. In this manner, anterior cervical plates may be used with dimensions that are smaller than conventional plates to avoid complications for patients.

Additional features and advantages will be set forth in the detailed description which follows, and in part will be readily apparent to those skilled in the art from that description or recognized by practicing the embodiments as described herein, including the detailed description that follows, the claims, as well as the appended drawings.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF THE FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIGS. 1F(1) and 1F(2) are left-side sectional views of the first and the second vertebrae, the anterior cervical plate (shown here unanchored), and the placement jig of FIGS. 1A-1D showing an exemplary initial position and an exemplary desired position of the anterior cervical plate along a cranial-caudal axis;

FIGS. 2H(1) and 2I(1) are a top-rear perspective view and a left-side view, respectively, of a circular cross-sectional area of a distal portion of the placement jig of FIG. 2A;

FIGS. 2H(2) and 2I(2) are a top-rear perspective view and a left-side view, respectively, of a rectangular cross-sectional area of a second embodiment of a distal portion of the placement jig of FIG. 2A;

FIGS. 2H(3) and 2I(3) are a top-rear perspective view and a left-side view, respectively, of multi-corner cross-sectional area of a third embodiment of a distal portion of the placement jig of FIG. 2A;

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Embodiments disclosed herein include placement jigs for osteosynthesis systems and related methods. Medical intervention may require fusing vertebrae of a diseased spinal column together. This often includes securing an interbody within an intervertebral space and anchoring an anterior cervical plate to the vertebrae. A placement jig may be received through the plate, removably coupled to the secured interbody with a press fit coupling, and used to abut the plate against the vertebrae to hold desired plate positioning so the plate may be anchored to the vertebrae with precision. By positioning the plate relative to the interbody using the placement jig, higher stress concentrations causing undesirable loosening associated with a misaligned plate may be avoided. In this manner, the useful life of the plate within a patient may be lengthened.

Figure 1A:
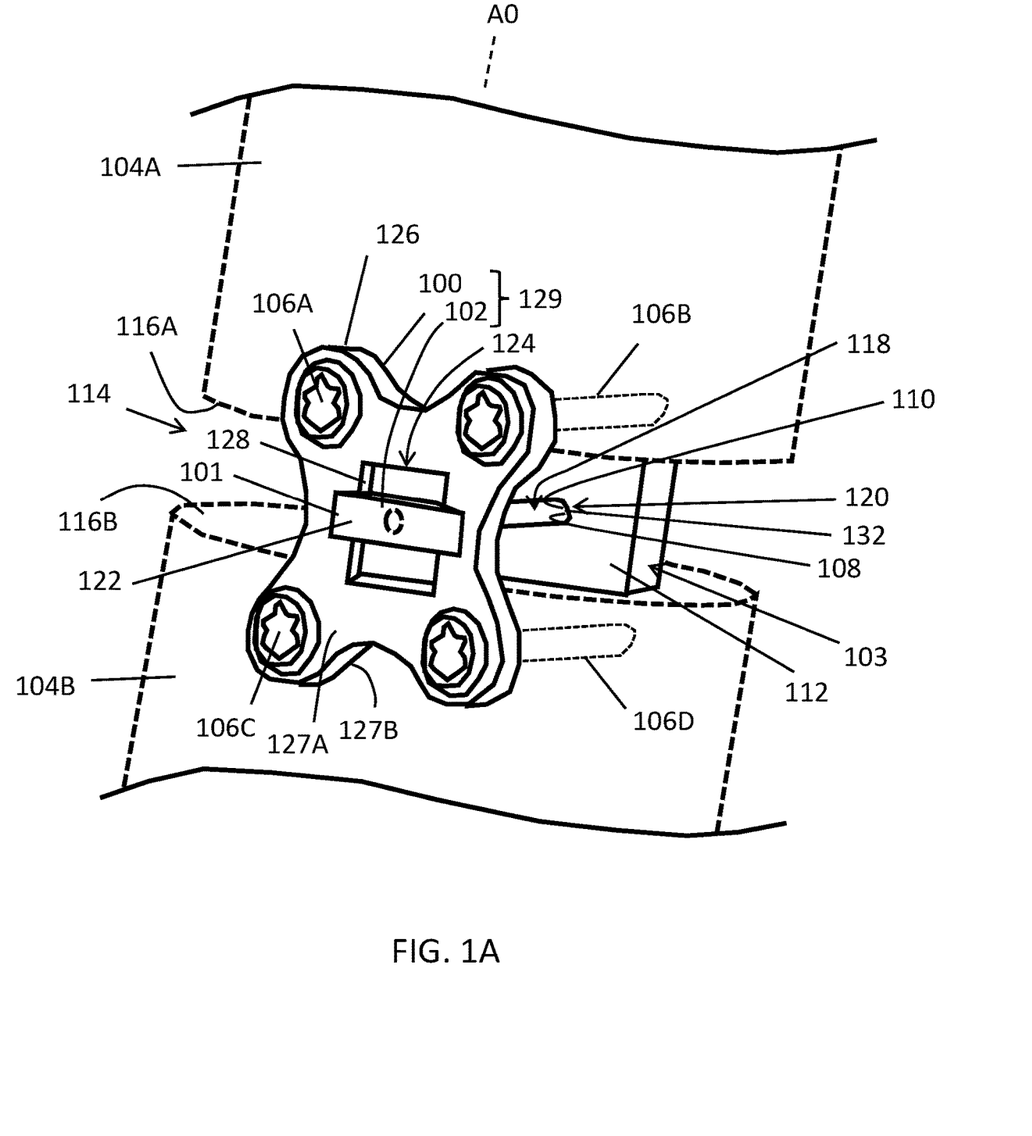
FIGS. 1A through 1D are a top perspective front view, left-side exploded view, front view, and left-side sectional view respectively of an interbody secured in an intervertebral space disposed between first and second vertebrae, and an exemplary osteosynthesis system, wherein the system includes an anterior cervical plate anchored to the vertebrae and an exemplary placement jig removably coupled to the interbody and abutting against the anterior cervical plate.

In this regard, FIG. 1A is a top perspective front view of an anterior cervical plate 100 aligned by an exemplary jig body 101 of a placement jig 102 relative to first and second vertebrae 104A, 104B and then subsequently secured to the first and second vertebrae 104A, 104B with anchors 106A, 106B, 106C, 106D that have been implanted into the first and the second vertebrae 104A, 104B. The placement jig 102 may guide the anterior cervical plate 100 to a desired position D2 (FIG. 1F(2)) and hold the anterior cervical plate 100 at that position until the anterior cervical plate 100 is anchored to be immovable relative to the first and the second vertebrae 104A, 104B.

In order to guide and hold the anterior cervical plate 100, the placement jig 102 includes features configured to be fastened to a static reference structure 103 and work with other features to guide (and hold) the location of the anterior cervical plate 100 relative to the static reference structure. As shown in FIG. 1A, the static reference structure 103 may be a recess 108 (e.g. "interbody insertion hole") formed from an interbody inner surface 110 of an interbody 112 (also known as "interbody cage"). As part of a medical intervention the interbody 112 replaces at least a portion of an intervertebral disc (not shown) that has been removed. As such, the interbody 112 is disposed within an intervertebral space 114 between the first and the second vertebrae 104A, 104B and may be secured as static by abutting against endplates 116A, 116B of the first and the second vertebrae 104A, 104B. A distal portion 118 of the placement jig 102 may be received by the recess 108 to be fastened to the interbody inner surface 110 by a removable coupling 120 (e.g. press fit coupling 132). This coupling allows the placement jig 102 to cantilever from the static reference structure 103, here the interbody 112, towards the anterior cervical plate 100. In this manner, the placement jig 102 may be fastened to the static reference structure 103.

As to other features of the placement jig 102 to guide the anterior cervical plate 100, the placement jig 102 includes a proximal portion 122 having a lateral width Z2 (FIG. 1C) configured to be larger than a lateral width Z0 (FIG. 1C) of a plate passageway 124 of a plate body 126 of the anterior cervical plate 100. The plate body 126 includes a rear surface 127B configured to abut against the first and the second vertebrae 104A, 104B, a front surface 127A opposite the rear surface 127B, and a plate inner surface 128 connecting the front and rear surfaces 127A, 127B and forming the plate passageway 124. The differences in width enable the distal portion 118 of the placement jig 102 to be received through the plate passageway 124 of the anterior cervical plate 100 and then received by the recess 108 of the interbody 112 where the distal portion 118 establishes the removable coupling 120. The surgeon with an initial insertion force FI1 (FIG. 5B) may move the distal portion 118 of the placement jig 102 to a desired depth within the recess 108 of the interbody 112 to thereby abut the anterior cervical plate 100 against the first and the second vertebrae 104A, 104B as the anterior cervical plate 100 may be disposed between the first and the second vertebrae 104A, 104B and the larger size of the lateral width Z2 (FIG. 1C) of the proximal portion 122 of the placement jig 102. In this manner, the placement jig 102 may guide and hold the anterior cervical plate 100.

Figure 1B:
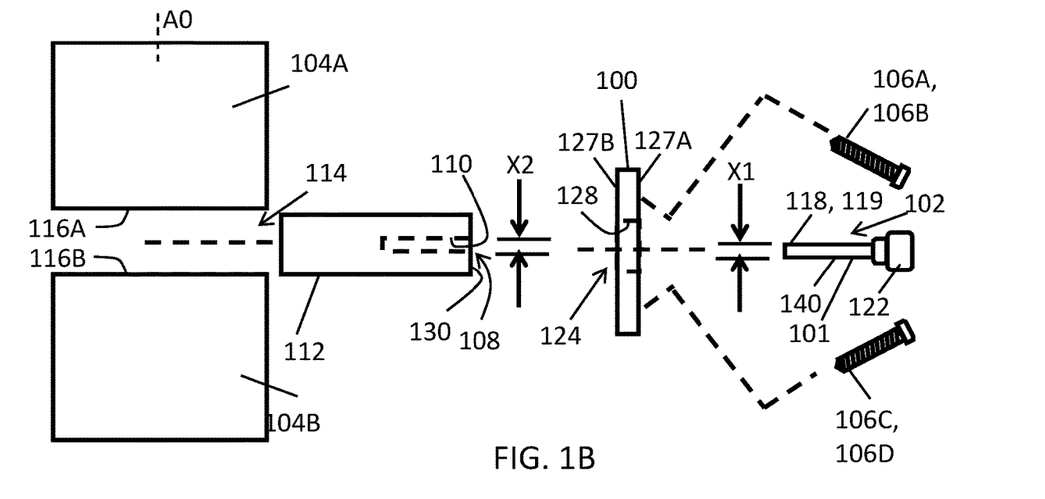
Figure 1C:
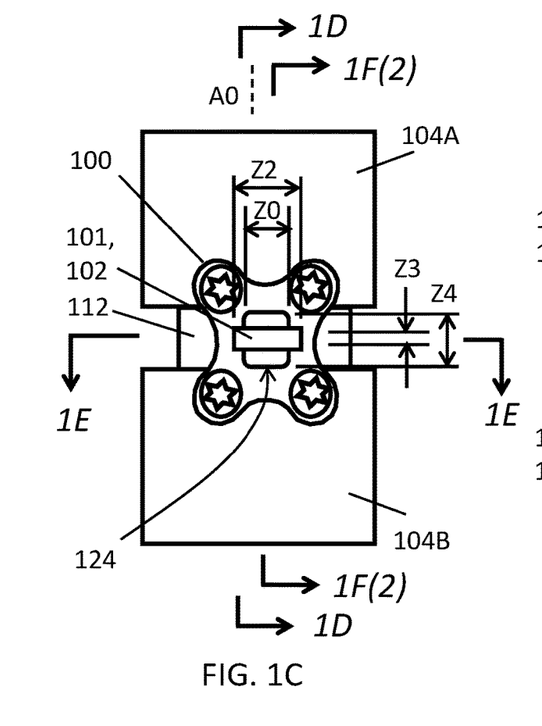
Figure 1D:
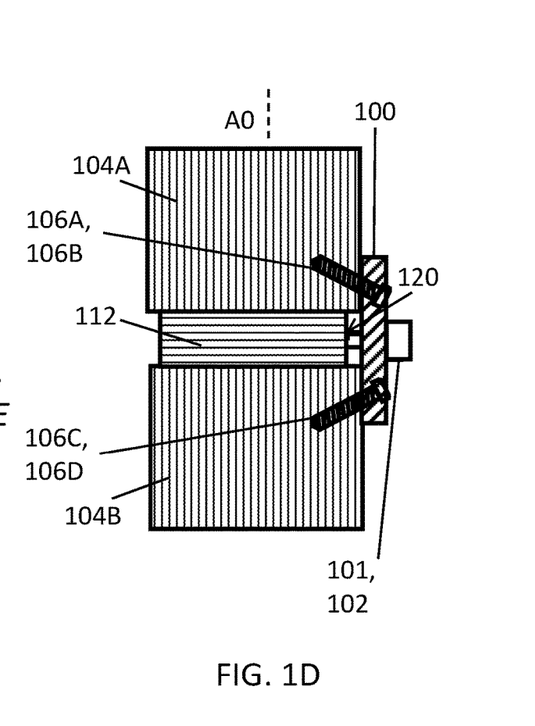

After guiding the anterior cervical plate 100 to the desired position D2 (FIG. 1F(2)), the anterior cervical plate 100 may be anchored to the first and the second vertebrae 104A, 104B with anchors 106A-106D. FIGS. 1B through 1D are left-side exploded view, front view, and left-side sectional view respectively of the interbody 112 secured in the intervertebral space 114 disposed between first and second vertebrae 104A, 104B, and an exemplary osteosynthesis system 129, wherein the osteosynthesis system 129 includes the anterior cervical plate 100 and the placement jig 102. The placement jig 102 is illustrated as removably coupled to the interbody 112 and abutting against the anterior cervical plate 100. In this manner, the anterior cervical plate 100 may be secured to the first and the second vertebrae 104A, 104B.

It is noted that the placement jig 102 may be free from abutting an external surface 130 of the interbody 112, and so the flexibility of selecting depths of the distal portion 118 within the interbody 112 may be possible without mechanical interference from the external surface 130 of the interbody 112. In this manner, features of the placement jig 102 may be used to guide or hold the anterior cervical plate 100.

Figure 1E:
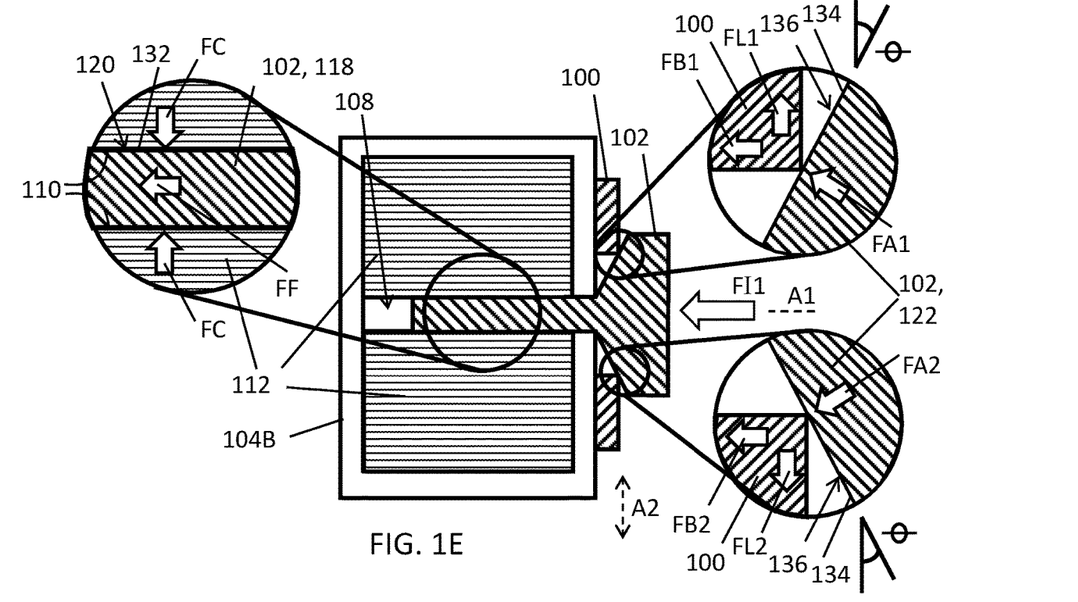
FIG. 1E is a top sectional view of the second vertebra, the anterior cervical plate (shown here unanchored to the vertebrae), and the placement jig of FIGS. 1A-1D wherein close-ups are also provided of a removable coupling between the placement jig and the interbody, and abutments between the placement jig and the anterior cervical plate.
Figure 1F:
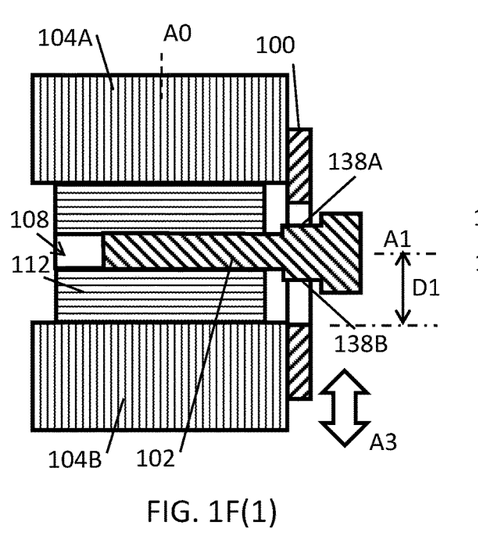

Details of relationships and forces between the placement jig 102 and the interbody 112 and the anterior cervical plate 100 are now discussed. FIG. 1E is a top sectional view of the second vertebra 104B, the anterior cervical plate 100 (shown here unanchored to the vertebrae), and the placement jig 102 of FIGS. 1A-1D wherein close-ups are also provided of the removable coupling 120 between the placement jig 102 and the interbody 112 and abutments between the placement jig 102 and the anterior cervical plate 100.

With continued reference to FIG. 1E, the removable coupling 120 may be generated using various forces created by features of the distal portion 118. As to the close-up of the removable coupling 120 between the placement jig 102 and the recess 108 of the interbody 112, the distal portion 118 of the placement jig 102 forms the removable coupling 120 as a press fit coupling 132 as the distal portion 118 of the placement jig 102 may include a width X1 (FIG. 1B) that may be substantially equal to or larger than a width X2 (FIG. 1B) of the recess 108 of the interbody 112. The relative size of the width X1 of the distal portion 118 results in a compression force FC (FIG. 1E) upon the distal portion 118 from the interbody inner surface 110 when the recess 108 of the interbody 112 receives the distal portion 118. This may be achieved by the surgeon applying the initial insertion force FI1 (FIG. 5B) to insert the distal portion 118 into the recess 108 that overcomes any kinetic friction or other opposition forces resisting this insertion. Once the surgeon completes the insertion, the compression force FC generates a static friction force FF that maintains the distal portion 118 in a static position relative to the interbody 112. The surgeon may later remove or disengage the placement jig 102 by manually applying a removal force FR (FIG. 5F) to the proximal portion 122 of the placement jig 102 that overcomes the static friction force FF in a direction along a longitudinal axis A1 of the placement jig 102. The surgeon may manually apply the removal force FR (FIG. 5F) with a clamping device (e.g. hemostat or forceps) that is not shown in the figures. In this manner, the removable coupling 120 between the placement jig 102 and the interbody 112 may be achieved and later removed.

With continued reference to FIG. 1E, the removable coupling 120 also facilitates holding of the anterior cervical plate 100. Subsequent to removal of the initial insertion force FI1 and receipt of the distal portion 118 to a depth deep enough within the recess 108, the proximal portion 122 of the placement jig 102 may abut against the anterior cervical plate 100, and the anterior cervical plate 100 may abut against the first and the second vertebrae 104A, 104B. As shown in the close-ups of FIG. 1E, lateral contact surfaces 134 of the proximal portion 122 of the placement jig 102 abut against the anterior cervical plate 100 to convey abutment forces FA1, FA2 to the anterior cervical plate 100. The abutment forces FA1, FA2 have component forces FB1, FB2 that direct the anterior cervical plate 100 against the first and the second vertebrae 104A, 104B and prevent separation of the anterior cervical plate 100 from the first and the second vertebrae 104A, 104B that may misalign the anterior cervical plate 100 from a desired position. In this manner, the removable coupling 120 may guide and hold the anterior cervical plate 100 in the desired position.

With continued reference to FIG. 1E, features of the proximal portion 122 also enable guiding the anterior cervical plate 100 in a lateral direction A2. As shown in FIG. 1E, the lateral contact surfaces 134 of the proximal portion 122 may include a tapered shape 136 having a taper angle Θ (theta) that may be in a range from ten (10) to fifty (50) degrees. The taper angle Θ (theta) may be measured relative to a direction normal to the longitudinal axis A1 of the placement jig 102 or may be measured relative to the lateral direction A2. The tapered shape 136 directs lateral forces FL1, FL2 that are components of the abutment forces FA1, FA2 conveyed from the proximal portion 122 to the anterior cervical plate 100. The lateral forces FL1, FL2 guide the anterior cervical plate 100 in the lateral direction A2 and resist misalignment movements of the anterior cervical plate 100 in the lateral direction A2. Further, the tapered shape 136 provides flexibility to use the placement jig 102 with embodiments of the anterior cervical plate 100 with various sizes of the lateral width Z0 of the plate passageway 124. In this manner, the placement jig 102 may laterally guide the anterior cervical plate 100 and provide flexibility to be used with various anterior cervical plate 100 having different dimensions of the lateral width Z0 of the plate passageway 124.

Features of the proximal portion 122 enable positional adjustments of the anterior cervical plate 100 parallel to the cranial-caudal axis A0. FIGS. 1F(1) and 1F(2) are left-side sectional views of the first and second vertebrae 104A, 104B, the anterior cervical plate 100 (shown here unanchored), and the placement jig 102 of FIGS. 1A-1D showing an exemplary initial position D1 and the exemplary desired position D2 along the cranial-caudal axis A0. As depicted in FIGS. 1F(1) and 1F(2), the proximal portion 122 of the placement jig 102 includes superior and inferior surfaces 138A, 138B, separated apart by a cranial-caudal dimension Z3, that do not simultaneously abut against the anterior cervical plate 100. In other words, the cranial-caudal dimension Z3 of the proximal portion 122 may be smaller than a cranial-caudal dimension Z4 of the plate passageway 124. This situation allows a range of motion A3 of the anterior cervical plate 100 parallel to the cranial-caudal axis A0 so that the surgeon can adjust the position of the anterior cervical plate 100 to best benefit the individual situation of the patient. The range of motion A3 may be in a range from one (1) millimeter to fifteen (15) millimeters. In this manner, the placement jig 102 facilitates convenient adjustment of the anterior cervical plate 100 along the cranial-caudal axis A0.

There are several specific features of the placement jig 102. FIGS. 2A through 2G are top-front perspective, top, bottom, right-side, left-side, rear and front views, respectively, of the placement jig 102 of FIG. 1A. The placement jig 102 includes the proximal portion 122, a medial portion 140, and the distal portion 118. Each of these will now be discussed sequentially with additional details.

First, the proximal portion 122 abuts against the anterior cervical plate 100 and the proximal portion 122 has the lateral width Z2 greater than the lateral width Z0 of the plate passageway 124. The lateral width Z2 of the proximal portion may be in a range from 1.5 centimeters to 3.5 centimeters. The lateral width Z2 permits the placement jig 102 to be used with many types of anterior cervical plate 100 having a different sizes of the lateral width Z0 of the plate passageway 124, as a wide variety sizes of anterior cervical plate 100 types may abut anywhere against the tapered shape 136 of the placement jig 102. Also, the cranial-caudal dimension Z3 of the proximal portion 122 may be increased to better enable the proximal portion 122 to to conform to a perimeter of the plate passageway 124 of the anterior cervical plate 100 and thereby provide resistance to undesirable rotations of the anterior cervical plate 100 into misalignment positions. Also, the proximal portion 122 may be comprised of a material (e.g. hard polyurethane, titanium, etc.) that is sufficiently strong and resilient to abut against the anterior cervical plate 100. In this manner, the proximal portion 122 may be used with various types of the anterior cervical plate 100 and reduce the chance of undesirable rotation.

As to the medial portion 140, it connects the proximal portion 122 to the distal portion 118 along the longitudinal axis A1 of the placement jig 102. During insertion of the distal portion 118 into the recess 108 of the interbody 112, the medial portion 140 conveys the initial insertion force FI1 (FIG. 5B) from the proximal portion 122 to the distal portion 118 where it may overcome the friction force FF that resists placement of the distal portion 118 to a desired depth within the recess 108 for the situation of the patient. The medial portion 140 also serves to convey sufficient force from the distal portion 118 to the proximal portion 122 as the abutment forces FA1, FA1 are applied to the anterior cervical plate 100 to guide the anterior cervical plate 100 into a desired position or alignment. Also, the medial portion 140 serves to convey the removal force FR from the proximal portion 122 to the distal portion 118. As such, the medial portion 140 may be comprised of a material (e.g. hard polyurethane, titanium, etc.) that is sufficiently strong and resilient to convey these forces without breaking. In this manner the medial portion 140 may connect the distal portion 118 and the proximal portion 122 as well as guide and hold the anterior cervical plate 100 in place.

As to the distal portion 118, the distal portion 118 includes a press fit surface 119 to removably couple with the interbody inner surface 110 forming the recess 108 of the interbody 112. As such the distal portion 118 may include a material (e.g. hard polyurethane, titanium, etc.) that is strong to resist compression of the interbody 112 while received in the recess 108, yet also strong to resist tensile forces without cracking. The distal portion 118 in combination with the medial portion 140 may extend a distance Z1 (FIG. 2D) from the proximal portion 122 along the longitudinal axis A1 of the placement jig 102. The distance Z1 may be in a range from one (1) centimeter to five (5) centimeters in order to extend into the recess 108. In this manner, the distal portion 118 may provide the removable coupling 120 with the interbody 112.

Figures 2A, 2B, 2C:
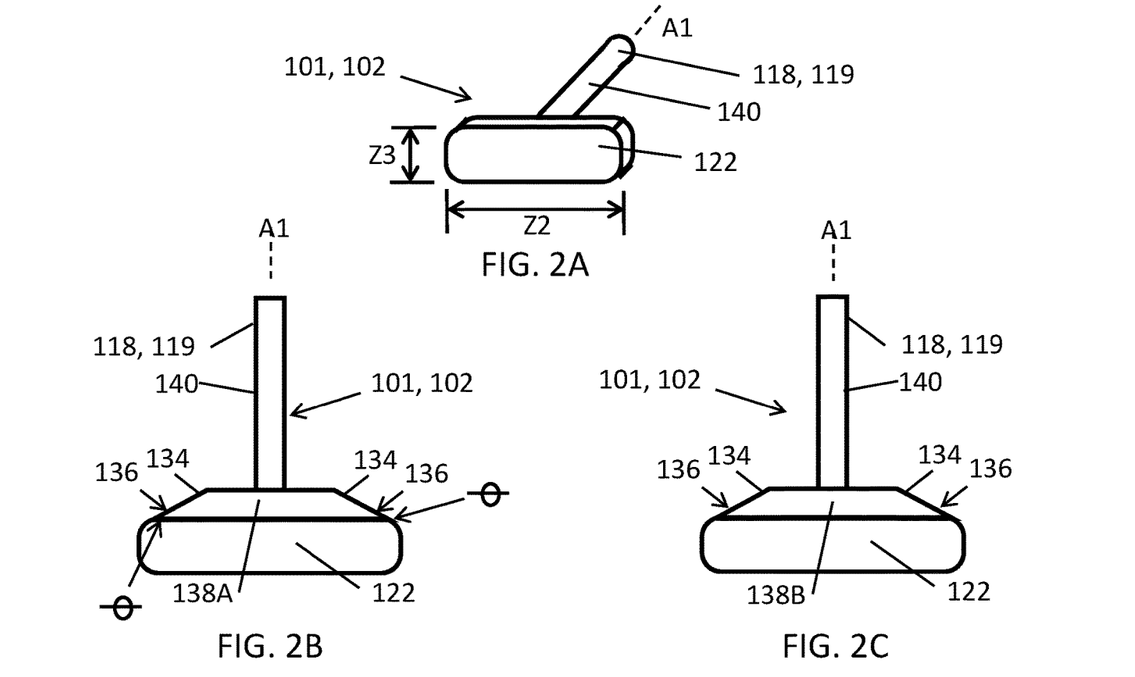
FIGS. 2A through 2G are top-front perspective, top, bottom, right-side, left-side, rear and front views, respectively, of the placement jig of FIG. 1A.
Figure 2D:
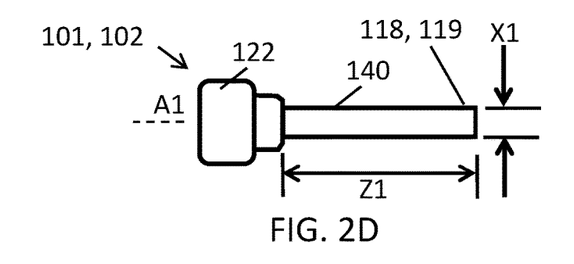
Figure 2E:
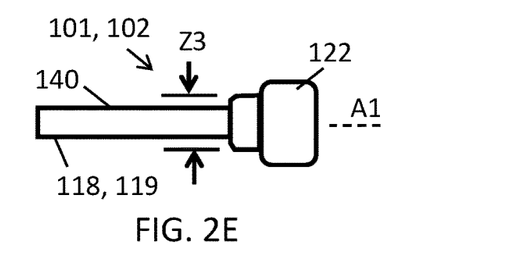
Figure 2F:
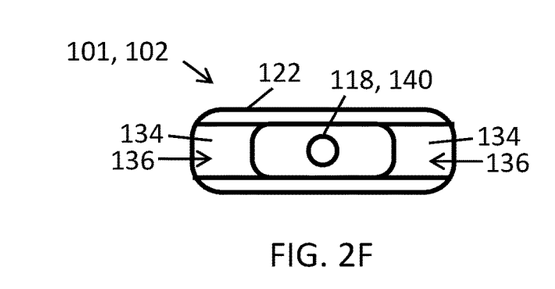
Figure 2G:
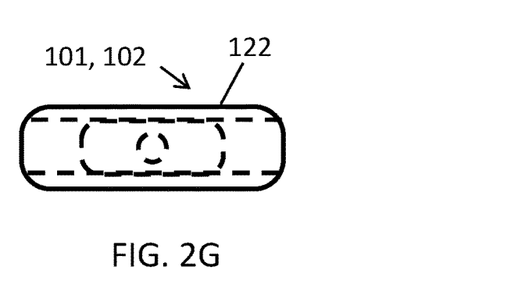
Figure 2H:
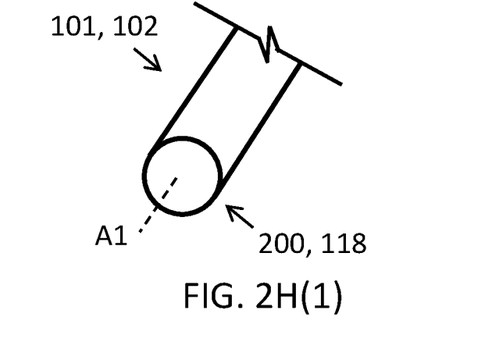
Figure 2I:
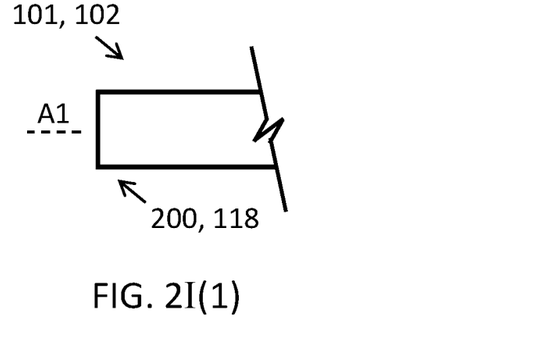

FIGS. 2H(1) and 2I(1) are a top-rear perspective view and a left-side view respectively of the distal portion 118 of the placement jig 102 of FIG. 2A. A circular cross-sectional area 200(1) of the distal portion 118 is illustrated and this shape may allow the distal portion 118 to further withstand higher values of the compression force FC (FIG. 1E) as stress will be more uniformly distributed along the circumference of the circular cross-sectional area 200(1).

FIGS. 2H(2) and 2I(2) are a top-rear perspective view and a left-side view respectively of a second embodiment of a distal portion 118(2) of the placement jig 102(2) of FIG. 2A. In this second embodiment, the distal portion 118(2) includes a rectangular cross-sectional area 200(2). This embodiment may be used to improve ease of insertion of the distal portion 118(2) into the recess 108 of the interbody 112 as compression and deformation during insertion will be more limited to the corners of the edges of the rectangular cross-sectional area 200(2). In this manner, compression and deformation during insertion may be limited to the multi-corners of the rectangular cross-sectional area 200(2) and this may improve insertion efficiency of the distal portion 118(2) into the recess 108 of the interbody 112.

FIGS. 2H(3) and 2I(3) are a top-rear perspective view and a left-side view respectively of a third embodiment of a distal portion 118(3) of the placement jig 102(3) of FIG. 2A. In this third embodiment, the distal portion 118(3) includes a multi-corner cross-sectional area 200(3). This embodiment may be used to improve ease of insertion of the distal portion 118(3) into the recess 108 of the interbody 112 as gaps are introduced as part of the multi-corner cross-sectional area 200(3) between the interbody inner surface 110 and the press fit surface 119 of the placement jig 102. In this manner, compression and deformation during insertion may be limited to the multi-corners of the cross-sectional area 200(3) and this may improve insertion efficiency of the distal portion 118(3) into the recess 108 of the interbody 112.

Figure 3A:
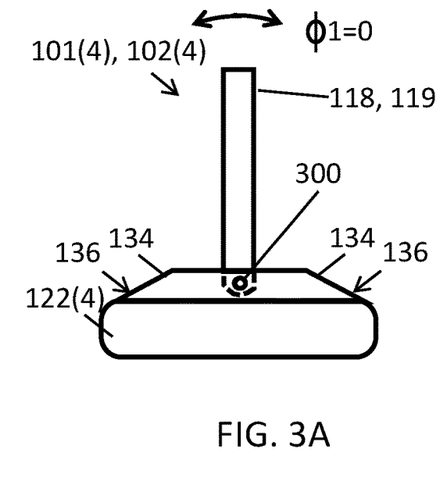
FIGS. 3A and 3B are top views of a fourth embodiment of a placement jig including a new embodiment of an exemplary proximal portion, wherein the proximal portion includes a pivot and the distal portion is shown in first and second angular positions respectively.
Figure 3B:
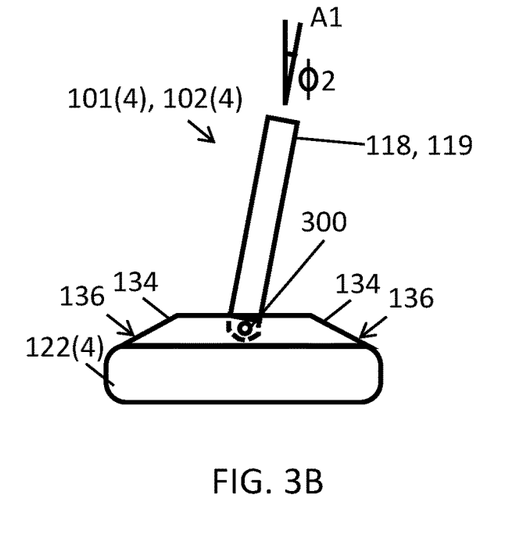
Figure 3C:
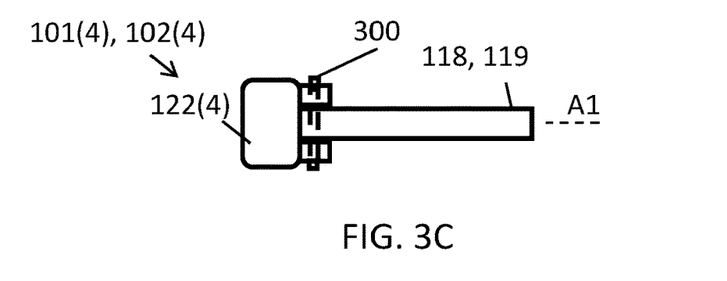
FIG. 3C is a right-side view of the placement jig of FIG. 3A.
Figure 3D:
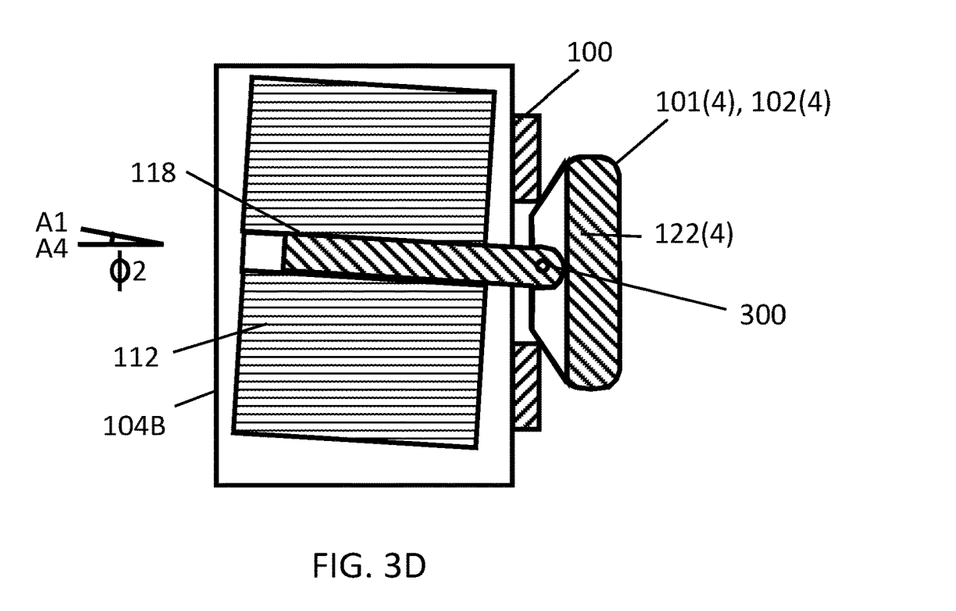
FIG. 3D is a top sectional view of the placement jig of FIG. 3A abutting against the anterior cervical plate of FIG. 1A, wherein the longitudinal axis A1 of the placement jig may be disposed at a different angular position than a center axis of the plate passageway.

FIGS. 3A and 3B are top views of a fourth embodiment of a placement jig 102(4) including a new embodiment of an exemplary proximal portion 122(4), wherein the proximal portion 122(4) includes a pivot 300 and the distal portion 118 is be shown in first and second angular positions Φ1 (phi 1), Φ2 (phi 2), respectively. Also, FIG. 3C is a right-side view of the placement jig 102(4) of FIG. 3A. In this embodiment the pivot 300 enables the proximal portion 122(4) to mate more symmetrically to the anterior cervical plate 100. The symmetry may facilitate anterior cervical plate 100 alignment to the proximal portion 122(4) and thereby facilitate better alignment of the anterior cervical plate 100 to the first and the second vertebrae 104A, 104B. This better alignment is despite, as shown in FIG. 3D, the longitudinal axis A1 of the placement jig 102(4) may be disposed at a different angular position than a center axis A4 of the plate passageway 124 of the anterior cervical plate 100. This is due to the longitudinal axis A1 of the placement jig 102 being secured to the interbody 112 at a different angular position than the center axis A4. In this manner using the pivot 300, symmetric alignment may be improved for different angular positions of the longitudinal axis A1 of the placement jig 102 relative to the anterior cervical plate 100.

Figure 4:
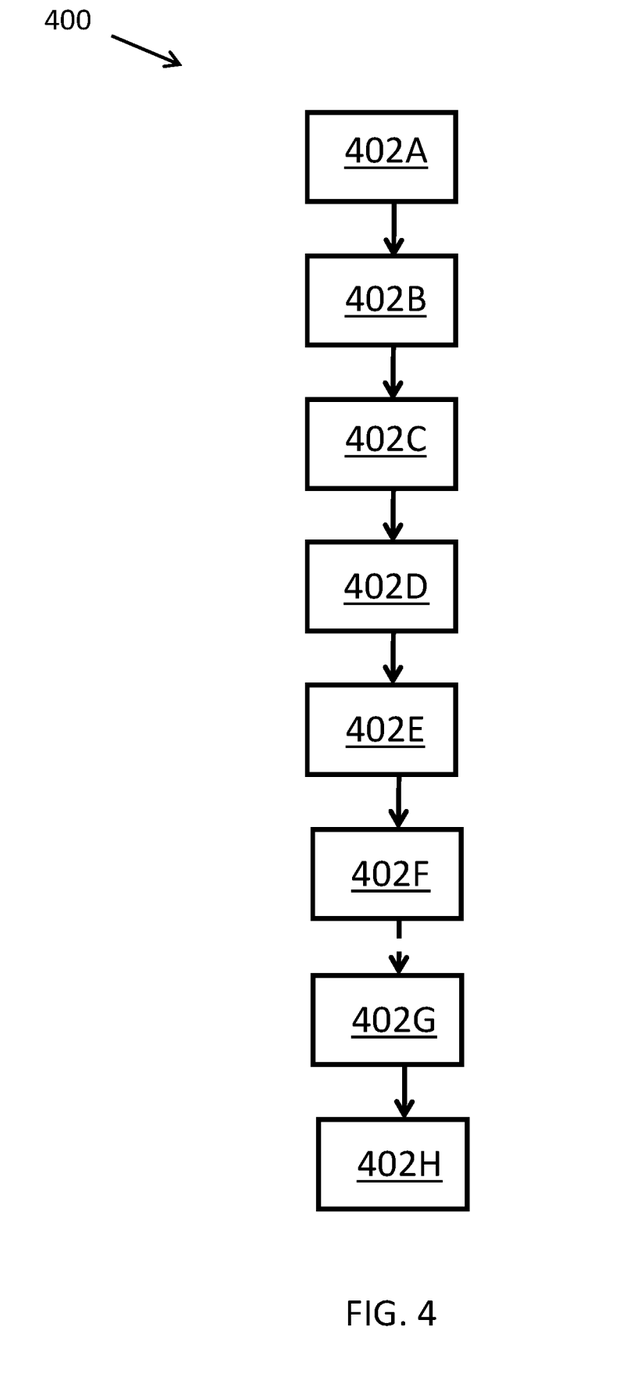
FIG. 4 is a flowchart of an exemplary method for positioning the anterior cervical plate of FIG. 1A with the placement jig prior to anchoring the anterior cervical plate to the first and second vertebrae.

FIG. 4 is a flowchart of an exemplary method 400 for positioning the anterior cervical plate 100 of FIG. 1A with the placement jig 102 disclosed herein. The method 400 is now discussed using the terminology discussed above and below in relation to the operations 402A through 402H as depicted in FIG. 4.

Figure 5A:
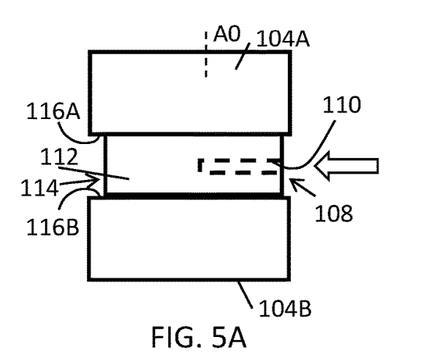
FIG. 5A is a left-side conceptual view of the interbody being disposed in the intervertebral space.

In this regard, FIG. 5A is relevant to operation 402A in that the method 400 may also include disposing the interbody 112 in the intervertebral space 114 and secured to the first and the second vertebrae 104A, 104B (operation 402A of FIG. 4). FIG. 5A is a left-side conceptual view of the interbody 112 being disposed and secured in the intervertebral space 114 as is known in the art. The interbody 112 may be installed in the intervertebral space 114 with an insertion device (not shown) that may engage with the interbody inner surface 110. Once the interbody 112 is secured, then the insertion device may disengage (e.g. by twisting out of a threaded coupling) with the interbody 112 and then the insertion device may be removed. There also may be mechanized features (not shown) of the interbody 112 that may direct the interbody 112 into the endplates 116A, 116B (FIG. 1A) of the vertebrae 104A, 104B to provide additional stability for the interbody 112. In this manner, the interbody 112 may be secured to the first and the second vertebrae 104A, 104B.

Figure 5B:
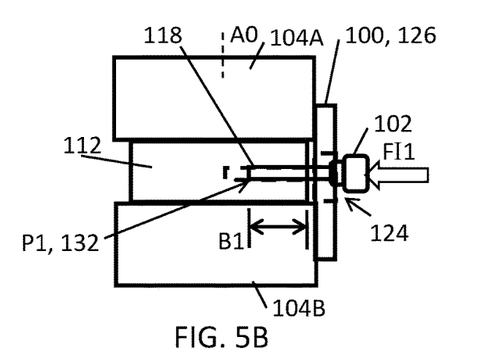
FIG. 5B is a left-side view of the placement jig being received through the anterior cervical plate and then being removably coupled to the interbody by the application of an initial insertion force, wherein the anterior cervical plate is disposed between the placement jig and the vertebrae.

FIG. 5B is relevant to operations 402B-402D. FIG. 5B is a left-side view of the placement jig 102 being received through the anterior cervical plate 100 and placed in abutment with the anterior cervical plate 100 of FIG. 5B. Consistent with FIG. 5B, the method 400 may also include receiving the distal portion 118 of the jig body 101 of the placement jig 102 through the plate passageway 124 of the anterior cervical plate 100, wherein the plate body 126 of the anterior cervical plate 100 includes the rear surface 127B (FIG. 1B) configured to abut against the first and the second vertebrae 104A, 104B, the front surface 127A (FIG. 1B) opposite the rear surface 127B (FIG. 1B), the plate inner surface 128 (FIG. 1B) connecting the front and rear surfaces 127A, 127B, and the plate inner surface 128 forms the plate passageway 124 (operation 402B of FIG. 4).

With continued reference to FIG. 5B, the method 400 may also include abutting the lateral contact surfaces 134 (FIG. 1E) of a proximal portion 122 of the placement jig 102 against the plate body 126, wherein the proximal portion 122 includes the lateral width Z2 (FIG. 1C) larger than the lateral width Z0 (FIG. 1C) of the plate passageway 124, wherein the medial portion 140 connects the distal portion 118 to the proximal portion 122 (operation 402C of FIG. 4).

With continued reference to FIG. 5B, the method 400 may also include removably coupling, by the press fit coupling 132, the press fit surface 119 (FIG. 1B) of the distal portion 118 to the interbody inner surface 110 (FIG. 1B) (operation 402D of FIG. 4). As shown in FIG. 5B, the application of the initial insertion force FI1 may facilitate the creation of the removable coupling 120 at a first press fit position P1.

Figure 5C:
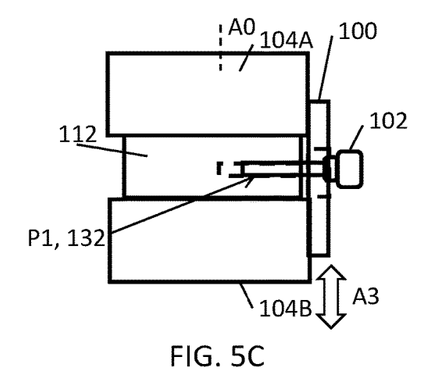
FIG. 5C is a left-side view of the anterior cervical plate of FIG. 5C being translated along the cranial-caudal axis to a more optimal position along the first and the second vertebrae, wherein the anterior cervical plate abuts against the placement jig and the first and second vertebrae.

FIG. 5C is relevant to operation 402E. FIG. 5C is a left-side view of the anterior cervical plate 100 of FIG. 5B being translated along the cranial-caudal axis A0 to a more optimal position along the first and the second vertebrae 104A, 104B, wherein the anterior cervical plate 100 is disposed between the placement jig 102 and the vertebrae 104A, 104B. The method 400 may also include this translating, while the distal portion 118 is disposed in the first press fit position P1. The anterior cervical plate 100 may translate parallel to the cranial-caudal axis A0 within the range of motion A3 from one (1) millimeter to fifteen (15) millimeters. As discussed previously, the proximal portion 122 includes the cranial-caudal dimension Z3 (FIG. 1C) smaller than the cranial-caudal dimension Z4 (FIG. 1C) of the plate passageway 124 and this facilitates the range of motion A3 (operation 402E of FIG. 4).

Figure 5D:
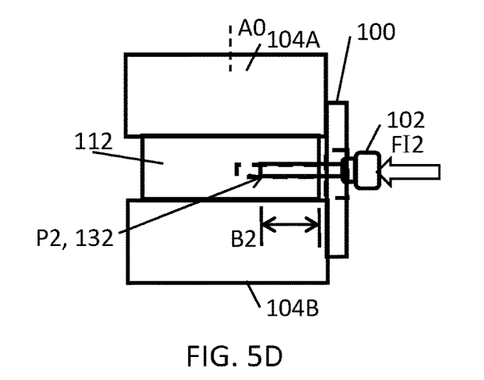
FIG. 5D is a left-side view of the anterior cervical plate of FIG. 5C with a second insertion force being applied to the placement jig in order to translate the placement jig to a second press fit position.

FIG. 5D is relevant to operation 402F. FIG. 5D is a left-side view of the anterior cervical plate 100 of FIG. 5C with a second insertion force FI2 being applied to the placement jig 102 in order to translate the placement jig 102 to a second press fit position P2. The method 400 may also include this application of the second insertion force FI2 to the placement jig 102 to translate the distal portion 118 parallel to the longitudinal axis A1 of the placement jig 102 from the first press fit position P1 to the second press fit position P2 relative to the interbody inner surface 110, and the second press fit position P2 is disposed at a deeper depth B2 within the interbody 112 than a depth B1 (FIG. 5B) associated with the first press fit position P1. The second press fit position P2 may result in increased component forces FB1, FB2 (FIG. 1E) related to improved holding of the anterior cervical plate 100 at the desired position. Accordingly, in the second press fit position P2 the anterior cervical plate 100 abuts against both the first and second vertebrae 104A, 104B and the proximal portion 122 (operation 402F of FIG. 4).

Figure 5E:
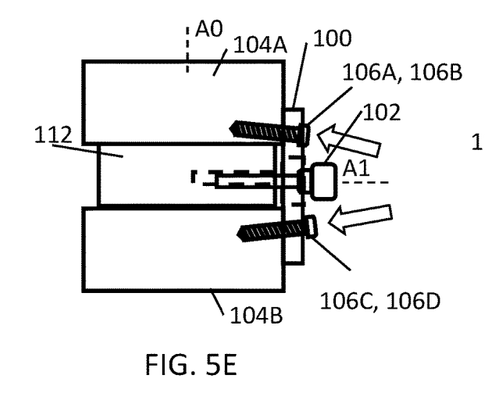
FIG. 5E is a left-side view of the anterior cervical plate of FIG. 5D in the more optimal position being anchored to the first and the second vertebrae.

FIG. 5E is relevant to operation 402G. FIG. 5E is a left-side view of the anterior cervical plate 100 of FIG. 5D in the desired position being anchored to the first and the second vertebrae 104A, 104B. The method 400 may also include securing the anterior cervical plate 100 to the first and the second vertebrae 104A, 104B with anchors 106A-106D (operation 402G of FIG. 4).

Figure 5F:
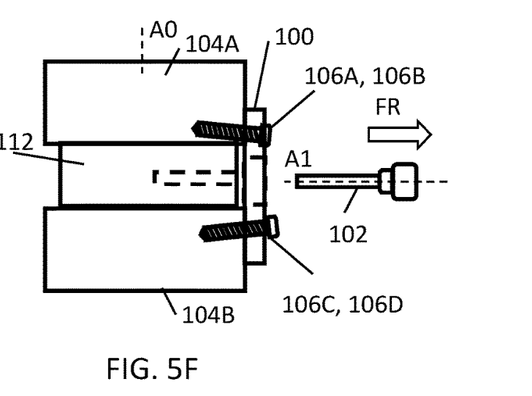
FIG. 5F is a left-side view of the anterior cervical plate of FIG. 5E anchored in the more optimal position while the placement jig is decoupled from the interbody and removed.

FIG. 5F is relevant to operation 402H. FIG. 5G is a left-side view of the anterior cervical plate 100 of FIG. 5E anchored in the desired position while the placement jig 102 is decoupled from the interbody 112 and removed by applying the removal force FR. The method 400 may also include removing the placement jig 102 (operation 402H of FIG. 4). The removal force FR may be applied, for example, using forceps (not shown) secured to the proximal portion 122. In this manner, the placement jig 102 may be removed.

Many modifications and other embodiments not set forth herein will come to mind to one skilled in the art to which the embodiments pertain having the benefit of the teachings presented in the foregoing descriptions and the associated drawings. Therefore, it is to be understood that the description and claims are not to be limited to the specific embodiments disclosed and that modifications and other embodiments are intended to be included within the scope of the appended claims. It is intended that the embodiments cover the modifications and variations of the embodiments provided they come within the scope of the appended claims and their equivalents. Although specific terms are employed herein, they are used in a generic and descriptive sense only and not for purposes of limitation.

What is claimed is:

1. An osteosynthesis system, comprising:
   an anterior cervical plate having a plate body including
      a rear surface configured to abut against first and second vertebrae,
      a front surface opposite the rear surface, and
      a plate inner surface connecting the front and the rear surfaces, wherein the plate inner surface forms a plate passageway; and
   a placement jig having a jig body including
      a distal portion including a press fit surface configured to be received through the plate passageway and to be removably coupled to an interbody inner surface of an interbody by a press fit coupling at first and second press fit positions, wherein the interbody inner surface forms a recess of the interbody, and wherein the interbody is disposed within an intervertebral space and secured to the first and the second vertebrae, wherein the distal portion is configured to translate along a longitudinal axis of the placement jig from the first press fit position to the second press fit position relative to the interbody inner surface, and the second press fit position is disposed at a deeper depth within the interbody than the first press fit position,
      a proximal portion including lateral contact surfaces having a lateral width configured to be larger than a lateral width of the plate passageway and the proximal portion configured to abut against the plate body, wherein in the second press fit position the anterior cervical plate abuts against the proximal portion and against the first and the second vertebrae, and
      a medial portion connecting the distal portion to the proximal portion and configured to be received through the plate passageway.

2. The system of claim 1, wherein the lateral contact surfaces include a tapered shape that widens with increasing distance from the medial portion.

3. The system of claim 2, wherein the tapered shape includes a taper angle in a range from 10 degrees to 50 degrees.

4. The system of claim 1, wherein the distal portion is configured to disengage from the interbody inner surface with a removal force applied by a surgeon to the proximal portion in a direction parallel to the longitudinal axis of the placement jig.

5. The system of claim 1, wherein the proximal portion includes a cranial-caudal dimension smaller than a cranial-caudal dimension of the plate passageway, so that when the distal portion is disposed in the first press fit position, the anterior cervical plate is configured to translate parallel to a cranial-caudal axis in a range of motion from one (1) millimeter to fifteen (15) millimeters.

6. The system of claim 1, wherein when the distal portion is disposed in the second press fit position the placement jig communicates with the interbody entirely through the interbody inner surface.

7. The system of claim 1, wherein the distal portion includes a circular cross-section shape.

8. The system of claim 1, wherein the distal portion includes a cross-sectional width in a range from 1.5 millimeters to 3.5 millimeters.

9. The system of claim 1, wherein the jig body includes hard polyurethane.

10. A placement jig having a jig body, the jig body comprising:
    a distal portion including a press fit surface configured to be received through a plate passageway of an anterior cervical plate and to be removably coupled to an interbody inner surface of an interbody by a press fit coupling at first and second press fit positions, wherein the interbody is disposed in an intervertebral space and secured to first and second vertebrae, wherein the distal portion is configured to translate along a longitudinal axis of the placement jig from the first press fit position to the second press fit position relative to the interbody inner surface, and the second press fit position is disposed at a deeper depth within the interbody than the first press fit position;
- a proximal portion including lateral contact surfaces having a lateral width configured to be larger than a lateral width of the plate passageway and the proximal portion configured to abut against a plate body of the anterior cervical plate, wherein the plate body includes a rear surface configured to abut against the first and the second vertebrae, a front surface opposite the rear surface, a plate inner surface connecting the front and the rear surfaces, wherein the plate inner surface forms the plate passageway; and
- a medial portion connecting the distal portion to the proximal portion and configured to be received through the plate passageway,
- wherein in the second press fit position the interior cervical plate is configured to abut against the proximal portion and against the first and the second vertebrae.

11. The placement jig of claim 10, wherein the lateral contact surfaces include a tapered shape that widens with increasing distance from the medial portion.

12. The placement jig of claim 11, wherein the tapered shape includes a taper angle in a range from 10 degrees to 50 degrees.

13. The placement jig of claim 10, wherein the distal portion is configured to disengage from the interbody inner surface with a removal force applied by a surgeon to the proximal portion in a direction parallel to the longitudinal axis of the placement jig.

14. The placement jig of claim 10, wherein the distal portion includes a circular cross-section shape.

15. The placement jig of claim 10, wherein the distal portion includes a cross-sectional width in a range from 1.5 millimeters to 3.5 millimeters.

16. The placement jig of claim 10, wherein the jig body includes hard polyurethane.

17. The placement jig of claim 10, wherein the proximal portion includes a cranial-caudal dimension smaller than a cranial-caudal dimension of the plate passageway, so that when the distal portion is disposed at the first press fit position, the proximal portion is configured to permit the anterior cervical plate to translate parallel to a cranial-caudal axis in a range of motion from one (1) millimeter to fifteen (15) millimeters.

18. A method, comprising:
- receiving a distal portion of a jig body of a placement jig through a plate passageway of an anterior cervical plate, wherein a plate body of the anterior cervical plate includes
  - a rear surface configured to abut against first and second vertebrae,
  - a front surface opposite the rear surface, and
  - a plate inner surface connecting the front and the rear surfaces, wherein the plate inner surface forms the plate passageway;
- removably coupling, by a press fit coupling, a press fit surface of the distal portion to an interbody inner surface of an interbody at a first press fit position, wherein the interbody is disposed in an intervertebral space and secured to the first and the second vertebrae; and
- applying an insertion force to the placement jig to translate the distal portion along a longitudinal axis of the placement jig from the first press fit position to a second press fit position relative to the interbody inner surface, wherein the second press fit position is disposed at a deeper depth within the interbody than the first press fit position, wherein in the second press fit position the anterior cervical plate abuts against lateral contact surfaces of a proximal portion of the jig body and against the first and the second vertebrae,
- wherein the proximal portion includes a lateral width larger than a lateral width of the plate passageway, and
- wherein a medial portion of the jig body connects the distal portion to the proximal portion.

19. The method of claim 18, further comprising
translating, while the distal portion is disposed in the first press fit position, the anterior cervical plate parallel to a cranial-caudal axis within a range of motion from one (1) millimeter to fifteen (15) millimeters, wherein the proximal portion includes a cranial-caudal dimension smaller than a cranial-caudal dimension of the plate passageway.

20. The method of claim 19, further comprising disengaging the distal portion from the interbody inner surface by applying a removal force to the proximal portion in a direction parallel to the longitudinal axis of the placement jig.

* * * * *